United States Patent [19]

Rijke

[11] Patent Number: 5,565,209
[45] Date of Patent: * Oct. 15, 1996

[54] ADJUVANT MIXTURE

[75] Inventor: Eric O. Rijke, Boxmeer, Netherlands

[73] Assignee: Akzo Nobel N.V., Arnhem, Netherlands

[*] Notice: The portion of the term of this patent subsequent to Jun. 25, 2008, has been disclaimed.

[21] Appl. No.: 717,437

[22] Filed: Jun. 19, 1991

Related U.S. Application Data

[63] Continuation-in-part of Ser. No. 414,648, Sep. 27, 1989, Pat. No. 5,026,543, which is a continuation of Ser. No. 168,287, Mar. 15, 1988, abandoned.

[30] Foreign Application Priority Data

Mar. 17, 1987 [NL] Netherlands .................... 87.00629

[51] Int. Cl.$^6$ .................... A61K 47/32; A61K 47/34; A61K 39/00
[52] U.S. Cl. .................... 424/423; 424/405; 514/772.6; 514/772.7
[58] Field of Search .................... 424/78.37, 486, 424/487, 88, 423; 514/723, 772.6, 772.7

[56] References Cited

U.S. PATENT DOCUMENTS

| | | |
|---|---|---|
| 3,178,350 | 4/1965 | Lund . |
| 3,869,546 | 3/1975 | Lund . |
| 3,919,411 | 11/1975 | Glass . |
| 4,567,042 | 1/1986 | Acree . |
| 4,567,043 | 1/1986 | Acree . |
| 4,606,918 | 8/1986 | Allison . |
| 4,772,466 | 9/1988 | Allison . |

OTHER PUBLICATIONS

Hunter et al., Journal of Immunology, vol. 127, No. 3, pp. 1244–1250 (1981).
Hunter et al., Journal of Immunology, vol. 133, No. 6, p. 3167–3175 (1984).

*Primary Examiner*—Edward J. Webman
*Attorney, Agent, or Firm*—Mary E. Gormley; William M. Blackstone

[57] ABSTRACT

According to the present invention oil-free vaccines are provided which contain polyoxypropylene-polyoxyethylene polyols as well as an acrylic acid polymer as adjuvating constituents. These vaccines were found to show excellent immunizing properties.

7 Claims, No Drawings

ADJUVANT MIXTURE

This is a continuation-in-part of application Ser. No. 07/414,648 filed Sep. 27, 1989, now U.S. Pat. No. 5,026,543, which is a File Wrapper Continuation of Ser. No. 07/168,287, filed Mar. 15, 1988, now abandoned.

The invention relates to an oil-free adjuvant mixture which contains polyoxypropylene/polyoxyethylene polyols, and to a vaccine which contains such an adjuvant mixture. For protection against transmittable infectious diseases it is usual to vaccinate humans and animals with immunogenic material against which protective antibodies can be formed.

For this purpose it is possible to administer, for example, the pathogen itself in live, but preferably non-infectious form, or the killed pathogen or an antigenic fraction of the pathogen in which the infectious component is missing.

In the last two cases it is necessary for one or more components which stimulate the immune response of the host to be protected to have been added to the antigen as well.

Such immunostimulatory components, usually termed adjuvants, are, inter alia, Freund's incomplete and complete adjuvant, *Corynebacterium parvum, Bordetella pertussis,* muramyl dipeptide, saponins, alhydrogel, trehalose dimycolate and mineral oils. However, all these adjuvants have disadvantages and most of them exhibit side effects such that routine use thereof is not permitted in humans or animals. Hunter et al. [R. Hunter, F. Strickland & F. Kézdy (1981) J. Immunol. 127 (3), 1244–1250; H. Snippe, M. J. de Reuver, F. Strickland, J. M. N. Willers and R. L. Hunter (1981), Int. Archs. Allergy appl. Immunol. 65, 390–398; R. L. Hunter and B. Bennett (1984) J. Immunol. 133, 3167–3175] described the use of non-ionic block polymers in vaccines.

These are surface-active substances halving a non-ionogenic base made up of a hydrophobic central section based on polyoxypropylene and hydrophilic ends based on polyoxyethylene (the so-called normal block polymers), or a hydrophylic central section based on polyoxyethylene and hydrophobic ends based on polyoxypropylene (the so-called reverse block polymers). The polymers concerned may be described by the respective general formulae:

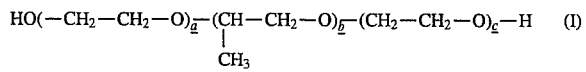

and

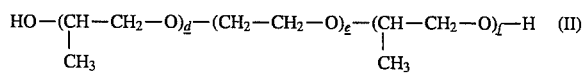

wherein a and c, or d and f may, if desired, be identical.

In addition to these so-called "triblock" copolymers, the use of so-called Tetronic$^{(R)}$ polyols as block polymer surfactants was described by Hunter & Bennett (1984). These are also termed "octablock" copolymers, and consist of a core of 4 polyoxypropylene or polyoxyethylene chains to which polyoxyethylene or polyoxypropylene chains respectivily are bonded at the 4 ends. These are the so-called T-type polyols.

The German patent publication No. 3,308,458 also describes the use of polyoxypropylene/polyoxyethylenepolyols as oil-free adjudants. It has been found that, although such adjuvants should in principle be suitable for it to be possible to safely administer them to humans and animals, the adjuvant action thereof is significantly less than, for example, the action of Freund's incomplete adjuvant.

The object of the present invention is therefore to provide an oil-free adjuvant mixture which is more potent than the above-named mixtures which contain only block-polymer polyoxypropylene/polyoxyethylene polyols.

The adjuvant according to the the invention is characterized in that, in addition to polyoxypropylene/polyoxyethylene block polymers it also contains at least one acrylic acid polymer.

Suitable polyoxypropylene/polyoxyethylene block polymers are, for example, known under the names Pluronic, Synperonic and Poloxamer.

The ratio of the hydrophobic to hydrophilic sections of said block polymers affects the physical constitution (liquid, paste or solid) to a considerable degree. The compounds from the Pluronic series which are suitable are, in particular, Pluronics from the liquid series (L, R or T) and the paste series (P), with the preference being for Pluronics from the liquid series. The preference for Pluronics from the liquid series is disposed towards Pluronic L 101, Pluronic L 121, Pluronic 25R 1, Pluronic 31R 1 and Pluronic T 1501.

The concentration of the block polymers in vaccines according to the invention is preferably approximately 0.1–10% on a weight basis, and in particular approximately 2.4–4.8% on a weight basis.

The term acrylic acid polymer means carbomers such as carboxypolymethylene or carboxyvinyl polymer.

Preferably, a polyacrylic acid is used which is crosslinked with polysaccharide, and in particular with polyallyl sucrose. The properties of such polyacrylic acids are determined by the number of carboxyl groups which is present in the final molecule. Suitable acrylic acid polymers are, for example, the substances which are known under the brand names Carbopol, Neocryl and Carboset. The preference is disposed towards Carbopols, such as Carbopol 934, Carbopol 907, Carbopol 910, Carbopol 940 and Carbopol 941.

The concentration of acrylic acid polymers in vaccine mixtures according to the invention is preferably 0.01–2% on a weight basis, and more particularly, 0.015–0.5% on a weight basis.

The ratio of the polyoxypropylene/polyoxyethylene block polymers to the acrylic acid polymers is preferably between 160:1 and 5:1, and in particular around approximately 16:1, on a weight basis.

As indicated above, the adjuvant mixtures according to the invention are suitable, in particular, for use in vaccines which contain non-living antigen material. This may be killed pathogens, or immunogenic fractions (subunits) thereof.

The pathogens may be, for example: viruses, bacteria, or parasites. These may be killed with chemical or physical agents. Here "killed" means inactivation, for example by a change in the genetic material and/or other vital constituents such that the pathogen is no longer capable of multiplying. Suitable chemical agents for killing pathogens are, for example, formaldehyde, glutaraldehyde, β-propiolactone, ethyleneimine and derivatives, or some other compounds which are capable of reacting in a bifunctional or multifunctional manner with reactive groups belonging to the pathogen. Physical agents for killing pathogens are, for example, UV radiation, gamma radiation, "heat shock" and X-ray radiation.

Antigen fractions of the above-named pathogens can be produced therefrom by means of chemical or physical decomposition methods, followed, if desired, by separation of a fraction by means of chromatography, centrifugation and similar techniques. In general low-molecular components are then obtained which, although very pure if desired, will also often have low immunogenic action. If desired, the low-molecular fractions of pathogens may be bonded to a carrier (for example, keyhole limpet haemocyanin or liposomes or other micellar complexes) to increase the immunogenicity. The abovementioned term "immunogenic fractions of pathogens" also means synthetic antigens or haptens, used to mimick natural antigens of the present pathogen. Such synthetic antigens or haptens can be prepared in a known manner by means of organic synthetic methods, or in the case of, for example, polypeptides, by means of recombinant DNA methods.

The concentration of antigen in a vaccine according to the invention is in general 1–95% on a weight basis.

In addition to such a vaccine which contains immunogenic material of only one pathogen (so-called monovalent vaccines), vaccines which contain immunogenic material of several pathogens (so-called combined vaccines) also belong to the invention as well. Such combined vaccines contain, for example, material from various viruses or from various strains of the same virus, or from virus/bacteria combinations or various bacteria.

EXAMPLE 1

Groups of 10 mice were vaccinated intramuscularly with 0.1 ml of adjuvant mixture containing inactivated Pseudorabies Virus (PRV) ($10^8$ $TCID_{50}$/ml). Blood samples were taken at 8 and 16 weeks after vaccination, after which antibody titres in the serum were determined by means of ELISA; the results are summarized in table 1.

TABLE 1

| Group | Adjuvant | Antibody response after 8 weeks | Antibody response after 16 weeks |
|---|---|---|---|
| 1 | none | 10.9 ± 0.9[a] | 9.9 ± 1.1 |
| 2 | Pluronic L 121[b] | 11.4 ± 2.1 | 11.1 ± 1.7 |
| 3 | Carbopol 934[c] | 14.0 ± 1.4 | 11.7 ± 2.1 |
| 4 | Pluronic L 121[b] + Carbopol 934[c] | 15.1 ± 0.8 | 14.0 ± 1.3 |

[a]mean ELISA titre ($^2$log) with standard deviation
[b]4,8% w/v
[c]0.15% w/v

EXAMPLE 2

Groups of 10 mice were vaccinated intramuscularly with 0.1 ml of adjuvant mixture containing inactivated PRV ($10^8$ $TCID_{50}$/ml). Blood samples were taken at 6 and 12 weeks after vaccination, after which antibody titres in the serum were determined by means of ELISA; the results are summarized in table 2.

TABLE 2

| Group | Adjuvant | Antibody response after 8 weeks | Antibody response after 16 weeks |
|---|---|---|---|
| 1 | none | 10.1 ± 1.0[a] | 9.2 ± 1.3 |
| 2 | Pluronic L 121[b] | 11.5 ± 1.4 | 11.0 ± 1.5 |
| 3 | Carbopol 940[c] | 11.7 ± 1.5 | 11.4 ± 1.1 |
| 4 | Pluronic L 121[b] + Carbopol 940[c] | 13.8 ± 1.6 | 13.2 ± 1.0 |

[a]mean ELISA titre ($^2$log) with standard deviation
[b]2,4% w/v
[c]0.015% w/v

Groups of 10 chickens were vaccinated intramuscularly with 0.5 ml of adjuvant mixture containing inactivated paramyxovirus ($P_3G$ strain) ($10^8$ $EID_{50}$/ml). Blood samples were taken at 4 weeks after vaccination. Antibody titres in the serum were determined by means of the haemagglutination inhibition test (HAR); the results are summarized in table 3.

TABLE 3

| Group | Adjuvant | Antibody response (HAR) 4 weeks after vaccination |
|---|---|---|
| 1 | none | 0.3 ± 1.0[a] |
| 2 | Carbopol 941[b] | 2.8 ± 2.2 |
| 3 | Carbopol 941[b] + Pluronic L 101[c] | 5.6 ± 1.0 |
| 4 | Pluronic L 101[c] | 0 ± 0 |
| 5 | Carbopol 940[b] | 2.4 ± 2.0 |
| 6 | Carbopol 940[b] + Pluronic L 101[c] | 5.5 ± 1.3 |

[a]mean HAR titre ($^2$log) with standard deviation
[b]0.075% w/v
[c]4.8% w/v

EXAMPLE 4

Groups of ten mice each were vaccinated intramuscularly with various dilutions of adjuvant containing inactivated PRV ($10^{8.0}$ $TCID_{50}$/ml). The mice were challenged 4 weeks after vaccination with virulent PRV (Phylaxia strain). The 50% protective doses were determined for the various adjuvants compositions as indicated in table 4.

TABLE 4

| Group | Adjuvant | $PD_{50}$ (µl) |
|---|---|---|
| 1 | mineral oil | 24.3 |
| 2 | Pluronic T 1501[a] | 4.0 |
| 3 | Carbopol 934[b] | 9.2 |
| 4 | Carbopol 934[b] + Pluronic T 1501[a] | 5.3 |

[a]2.4% w/v
[b]0.15% w/v

EXAMPLE 5

Groups of 7 or 8 pigs were vaccinated with inactivated PRV. The antibody response of the pigs 3 weeks after vaccination was determined by virus neutralization (VN) tests. The 50% protective dose of the various formulations was determined in mice as described in Example 4. The results are summarized in table 5.

TABLE 5

| Group | Adjuvant | $PD_{50}$ (µl) (mice) | VN titre ($^2$log) with standard deviation (pigs) |
|---|---|---|---|
| 1 | Carbopol 910[a] | 48.5 | 5.1 ± 2.4 |
| 2 | Pluronic T 1501[b] | 55.7 | 4.0 ± 2.3 |
| 3 | Carbopol 934[a] + Pluronic T 1501[b] | 33.0 | 5.5 ± 2.4 |

[a]0.5% w/v
[b]2.4% w/v

EXAMPLE 6

Analogous to the previous examples pigs were vaccinated against *Escherichia coli pilus* antigens with various vaccine compositions containing 55 µg K88ab antigen/ml. At 3 weeks post-vaccination the antibody response was measured by ELISA. The results are presented in table 6.

TABLE 6

| Group | Adjuvant | Antibody titre ($^2$log) with standard deviation |
|---|---|---|
| 1 | Pluronic T 1501[a] | 8.0 ± 1.2 |
| 2 | Carbopol 934[b] | 8.7 ± 1.0 |
| 3 | Pluronic T 1501[a] + Carbopol 934[b] | 9.7 ± 1.8 |

[a] 2.4% w/v
[b] 0.15% w/v

EXAMPLE 7

Groups of 8 mice were vaccinated intramuscularly with 0.1 ml of adjuvant compositions containing inactivated Pseudorabies virus ($10^8$ TCID$_{50}$/ml). Blood samples were taken 4 weeks after vaccination, after which antibody titres in the serum were determined by means of Elisa; the results are summarized in the table:

TABLE 7

| group | adjuvant | antibody response after 4 weeks |
|---|---|---|
| 1 | none | 10.7[a] ± 1.2 |
| 2 | Pluronic L121[b] | 11.1 ± 0.6 |
| 3 | Carbopol 910[c] | 12.9 ± 1.5 |
| 4 | Pluronic L121[b] + Carbopol 910[c] | 13.9 ± 0.5 |

[a] mean Elisa titre ($^2$log) with standard deviation (STUDENT'S T-test $p < 0.05$)
[b] 1.0% w/v
[c] 1.0% w/v

I claim:

1. Oil-free adjuvant mixture comprising an immunostimulatory amount of polyoxypropylene/polyoxyethylene block polymers having HLB values less than or equal to 2, and at least one acrylic acid polymer, wherein the ratio of block polymers to acrylic acid polymer is from 1000:1 to 0.05:1 on a weight basis.

2. Oil-free adjuvant mixture according to claim 1, comprising a high molecular weight polymer or copolymer of acrylic acid cross linked with allyl ether.

3. Vaccine comprising: about 0.11–12% by weight of an oil-free adjuvant mixture consisting of polyoxypropylene/polyoxyethylene block polymers having HLB values less than or equal to 2 and at least one acrylic acid polymer; and immunogenic material.

4. Vaccine comprising the adjuvant mixture of claim 1 in a quantity of about 1–30% based on the total weight of the vaccine.

5. Vaccine according to claim 4, comprising immunogenic material from an animal pathogen.

6. Vaccine according to claim 5, comprising a fowl pathogen as an animal pathogen.

7. An oil-free adjuvant mixture according to claim 1, wherein the ratio of block polymers to acrylic acid polymer is from approximately 320:1 to approximately 1:1 on a weight basis.

* * * * *

UNITED STATES PATENT AND TRADEMARK OFFICE
CERTIFICATE OF CORRECTION

PATENT NO. : 5,565,209
DATED : OCTOBER 15, 1996
INVENTOR(S) : Eric O. Rijke

It is certified that error appears in the above-indentified patent and that said Letters Patent is hereby corrected as shown below:

Column 3, line 63 insert --EXAMPLE 3--.

Signed and Sealed this

Twenty-eighth Day of January, 1997

Attest:

BRUCE LEHMAN

*Attesting Officer*    *Commissioner of Patents and Trademarks*